United States Patent [19]

Tice et al.

[11] Patent Number: 5,407,609

[45] Date of Patent: Apr. 18, 1995

[54] MICROENCAPSULATION PROCESS AND PRODUCTS THEREFROM

[75] Inventors: Thomas R. Tice; Richard M. Gilley, both of Birmingham, Ala.

[73] Assignee: Southern Research Institute, Birmingham, Ala.

[21] Appl. No.: 62,696

[22] Filed: May 17, 1993

Related U.S. Application Data

[63] Continuation of Ser. No. 347,476, May 4, 1989, abandoned.

[51] Int. Cl.$^6$ ............................................. B01J 13/12
[52] U.S. Cl. ...................................... 264/46; 264/4.1; 427/213.3; 427/213.36
[58] Field of Search ................................ 264/4.1, 4.6; 427/213.3, 213.36; 424/490, 491, 497; 428/402.21, 402.22, 402.24

[56] References Cited

U.S. PATENT DOCUMENTS

| | | | |
|---|---|---|---|
| 3,644,963 | 5/1972 | Pasin | 424/497 X |
| 3,780,195 | 12/1973 | Balassa | 264/4.6 X |
| 3,790,497 | 2/1974 | Sato et al. | 264/4.3 |
| 3,943,063 | 3/1976 | Morishita et al. | 428/402.2 X |
| 4,089,800 | 5/1978 | Temple | 424/497 X |
| 4,389,330 | 6/1983 | Tice et al. | 424/497 X |
| 4,572,869 | 2/1986 | Wismer et al. | 428/402.24 |
| 4,637,905 | 1/1987 | Gardner | 428/402.2 X |
| 4,652,441 | 3/1987 | Okada et al. | 428/402.2 X |
| 4,675,189 | 6/1987 | Kent et al. | 424/490 |
| 4,782,097 | 11/1988 | Jain et al. | 521/56 |
| 4,818,542 | 4/1989 | DeLuca et al. | 424/491 |
| 4,897,268 | 1/1990 | Tice et al. | 424/455 |
| 4,933,105 | 6/1990 | Fong | 424/497 X |
| 4,994,281 | 2/1991 | Muranishi et al. | 424/497 |
| 5,075,109 | 12/1991 | Tice et al. | 428/402.21 |

FOREIGN PATENT DOCUMENTS

| | | | |
|---|---|---|---|
| 0274961 | 7/1988 | European Pat. Off. | 264/4.6 |
| 0275796 | 7/1988 | European Pat. Off. | 264/4.6 |
| 2930248 | 2/1981 | Germany | B01J 13/02 |

OTHER PUBLICATIONS

C. Bindschaedler et al., "Polyanhydride Microsphere Formulation by Solvent Extraction", *J of Phar. Sci.*, 77:696–698 (1988).

E. Mathiowitz et al., "Polyanhydride Microspheres as Drug Carriers", *J. of Appl. Polymer Sci.*, 35:755–774 (1988).

Toyomi Sato et al., "Porous Bidoegradable Microspheres for Controlled Drug Delivery", *Pharm. Research*, 5:21–30 (1988).

*Primary Examiner*—Robert L. Stoll
*Assistant Examiner*—John M. Covert
*Attorney, Agent, or Firm*—Needle & Rosenberg

[57] ABSTRACT

A method of microencapsulating an agent to form a microencapsulated product, having the steps of dispersing an effective amount of the agent in a solvent containing a dissolved wall forming material to form a dispersion, combining the dispersion with an effective amount of a continuous process medium to form an emulsion that contains the process medium and microdroplets having the agent, the solvent and the wall forming material and adding rapidly the emulsion to an effective amount of an extraction medium to extract the solvent from the microdroplets to form the microencapsulated product.

73 Claims, No Drawings

MICROENCAPSULATION PROCESS AND PRODUCTS THEREFROM

This application is a continuation of application Ser. No. 07/347,476, filed May 4, 1989, now abandoned.

BACKGROUND OF THE INVENTION

1. Field of the Invention

The present invention relates to a method to prepare microcapsules, microspheres, nanocapsules and nanospheres. More particularly, the present invention relates to an emulsion-based method for preparing microcapsules or microspheres containing water-soluble or oil-soluble agents, particularly highly water-soluble agents.

2. Description of the Prior Art

Microcapsules and microspheres are usually powders consisting of spherical particles 2 millimeters or less in diameter, usually 500 microns or less in diameter. If the particles are less than 1 micron, they are often referred to as nanocapsules or nanospheres. For the most part, the difference between microcapsules and nanocapsules is their size; their internal structure is about the same. Similarly, the difference between microspheres and nanospheres is their size; their internal structure is about the same.

A microcapsule (or nanocapsule) has its encapsulated material, herein after referred to as agent, centrally located within a unique membrane, usually a polymeric membrane. This membrane may be termed a wall-forming material, and is usually a polymeric material. Because of their internal structure, permeable microcapsules designed for controlled-release applications release their agent at a constant rate (zero-order rate of release). Also, impermeable microcapsules can be used for rupture-release applications. Hereinafter, the term microcapsule will include nanocapsules, microbubbles (hollow particles), porous microbubbles and particles in general that comprise a central core surrounded by a unique outer membrane.

A microsphere has its agent dispersed throughout the particle; that is, the internal structure is a matrix of the agent and excipient, usually a polymeric excipient. Usually controlled-release microspheres release their agent at a declining rate (first-order). But microspheres can be designed to release agents at a near zero-order rate. Microspheres tend to be more difficult to rupture as compared to microcapsules because their internal structure is stronger. Hereinafter, the term microsphere will include nanospheres, microparticles, nanoparticles, microsponges (porous microspheres) and particles in general, with an internal structure comprising a matrix of agent and excipient.

A wide variety of methods to prepare microcapsules and microspheres are described in the literature. Several of these methods make use of emulsions to make microspheres, in particular to make microspheres less than 2 millimeters in diameter. To give a general example of such processes, one can dissolve a polymer in a suitable organic solvent (the polymer solvent), dissolve or disperse an agent in this polymer solution, disperse the resulting polymer/agent mixture into an aqueous phase (the processing medium) to obtain an oil-in-water emulsion with oil microdroplets dispersed in the processing medium, and remove the solvent from the microdroplets to form microspheres. These processes can also be performed with water-in-oil emulsions and with double emulsions.

The use of emulsion-based processes that follow this basic approach is described in several U.S. patents. For example, U.S. Pat. No. 4,384,975 describes the production of microspheres by forming an emulsion and then slowly removing the polymer solvent from the microdroplets in the emulsion by vacuum distillation. As another example, U.S. Pat. No. 3,891,570 discloses a method in which the polymer solvent is removed from the microdroplets in the emulsion by applying heat or reducing the pressure in the fabrication vessel. In still another example, U.S. Pat. No. 4,389,330, the polymer solvent is partially removed from the microdroplets in the emulsion by vacuum distillation (preferably 40 to 60% of the polymer solvent) and then the remainder of the polymer solvent is extracted to solidify the microspheres.

The disadvantage of the above-described processes, as with other emulsion-based processes, is that certain agents can partition into the processing medium, that is, the agents migrate out of the microdroplets during the polymer solvent removal step, resulting in a poor encapsulation efficiency. Furthermore, all of the above-described processes afford microspheres rather than microcapsules.

Another emulsion-based method to prepare microspheres described in U.S. Pat. No. 3,737,337 uses a controlled extraction of the polymer solvent from the microdroplets by adding processing medium to the emulsion at a controlled rate. However, this patent teaches away from the present invention by disclosing that the extraction must proceed slowly or no spherical particles will be formed. Similarly, U.S. Pat. No. 4,652,441 describes a method to encapsulate water-soluble agents from water-in-oil-in-water emulsions, and teaches that a high-viscosity, drug-retaining substance must be included in the inner water phase to retain the drug in the microdroplets during evaporation of the polymer solvent. U.S. Pat. No. 4,652,441 also teaches against the present invention by suggesting that it is impossible to effectively encapsulate water-soluble agents without using drug-retaining substances in the emulsion.

SUMMARY OF THE INVENTION

Accordingly, one object of the present invention is to provide an emulsion-based method for preparing microspheres with agents that have a high propensity to partition within minutes into the processing medium, the continuous phase of the emulsion. Yet another object of the present invention is a method to prepare microcapsules, as well as microspheres, from an emulsion. Yet another object of the invention is to provide a method for preparing microspheres or microcapsules containing an agent that has a solubility of greater than 10 milligrams per milliliter in the processing medium. Yet another object of the invention is to control the porosity of the wall of microcapsules or excipient of microspheres by controlling the rate of extraction of the solvent from the microdroplets of the emulsion. Yet another object of the present invention is to provide a method for making microcapsules and microspheres having diameters from less than 1 micron to greater than 2 millimeters. Still another object of the present invention is to provide a method for preparing drug-loaded microspheres and microcapsules that result in free-flowing powders of unagglomerated spherical particles suitable for parenteral as well as other routes of drug administration.

Briefly stated, this invention involves (1) dissolving or otherwise dispersing one or more agents (liquids or solids) in a solvent containing one or more dissolved wall-forming materials or excipients (usually the wall-forming material or excipient is a polymer dissolved in a polymer solvent); (2) dispersing the agent/polymer-solvent mixture (the discontinuous phase) into a processing medium (the continuous phase which is preferably saturated with polymer solvent) to form an emulsion; and (3) transferring all of the emulsion immediately to a large volume of processing medium or other suitable extraction medium to immediately extract the solvent from the microdroplets in the emulsion to form a microencapsulated product, such as microcapsules or microspheres. The particular features of this technique that distinguish its uniqueness are described below.

DETAILED DESCRIPTION OF THE PREFERRED EMBODIMENTS

One of the important features of this microencapsulation technique is the rate of polymer solvent removal from the microdroplets of the emulsion. By adding the emulsion to the processing medium all at once and thereby removing most of the polymer solvent very rapidly (within 3 minutes), agents highly soluble in the processing medium can be encapsulated as well as less soluble agents.

The existing literature on the microencapsulation of water-soluble agents teaches that water-soluble agents, especially if high loadings such as greater than 10 wt. % and particularly greater than 30 wt. % are desired, cannot be easily encapsulated by oil-in-water emulsion-based processes because of the tendency of the agent to migrate out of the organic microdroplets into the aqueous processing medium. This agent migration is greater with small emulsion microdroplets because of their increased surface area. The advantage of this invention over other emulsion-based processes is that highly water-soluble agents, such as agents with water solubilities as high as 2 grams per milliliter, can be effectively encapsulated at loadings of up to 80 wt. %. Moreover, the resultant microspheres or microcapsules are free-flowing powders of spherical particles. Depending on the processing conditions, these particles can have diameters ranging from less than 1 micron to greater than 2 millimeters.

To prepare microcapsules or microspheres by this invention, a suitable wall-forming material, such as a polymer, is first dissolved or otherwise dispersed in a solvent. The term wall-forming material also denotes unique membranes and excipients. The solvent used to dissolve the wall material or excipient can be selected from a variety of common organic solvents including halogenated aliphatic hydrocarbons such as methylene chloride, chloroform, and the like; alcohols; aromatic hydrocarbons such as toluene and the like; halogenated aromatic hydrocarbons; ethers such as methyl t-butyl ether and the like; cyclic ethers such as tetrahydrofuran and the like; ethyl acetate; diethyl carbonate; acetone; cyclohexane; and water. These solvents may be used alone or in combination. The solvent chosen must be a material that will dissolve the wall material or excipient and it is best that it is chemically inert with respect to the agent being encapsulated and the polymer. Moreover, the solvent must have limited solubility in the extraction medium. Generally, limited solubility means having a solubility from about 1 part per 100 to about 25 parts per 100.

Suitable wall-forming materials include, but are not limited to, poly(dienes) such as poly(butadiene) and the like; poly(alkenes) such as polyethylene, polypropylene, and the like; poly(acrylics) such as poly(acrylic acid) and the like; poly(methacrylics) such as poly(methyl methacrylate), poly(hydroxyethyl methacrylate), and the like; poly(vinyl ethers); poly(vinyl alcohols); poly(vinyl ketones); poly(vinyl halides) such as poly(vinyl chloride) and the like;, poly(vinyl nitriles), poly(vinyl esters) such as poly(vinyl acetate) and the like; poly(vinyl pyridines) such as poly(2-vinyl pyridine), poly(5-methyl-2-vinyl pyridine) and the like; poly(styrenes); poly(carbonates); poly(esters); poly(orthoesters); poly(esteramides); poly(anhydrides); poly(urethanes); poly(amides); cellulose ethers such as methyl cellulose, hydroxyethyl cellulose, hydroxypropyl methyl cellulose, and the like; cellulose esters such as cellulose acetate, cellulose acetate phthalate, cellulose acetate butyrate, and the like; poly(saccharides), proteins, gelatin, starch, gums, resins, and the like. These materials may be used alone, as physical mixtures (blends), or as copolymers. A preferred group of wall-forming materials includes biodegradable polymers such as poly(lactide), poly(glycolide), poly(caprolactone), poly(hydroxybutyrate), and copolymers thereof, including but not limited to poly(lactide-co-glycolide), poly(lactide-co-caprolactone) and the like.

The liquid, or solid agent to be encapsulated is then dispersed or dissolved in the solvent containing the dissolved wall-forming material or excipient. Examples of biological agents that may be encapsulated by this technique include, but are not limited to, analgesics such as acetaminophen, acetylsalicylic acid, and the like; anesthetics such as lidocaine, xylocaine, and the like; anorexics such as dexedrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erytromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, verapamil HCl, and the like; enzymes such as lactase, pancrelipase, succinic acid dehydrogenase, and the like; peptides and proteins such as LHRH, somatostatin, calcitonin, growth hormone, growth releasing factor, angiotensin, FSH, EGF, vasopressin, ACTH, human serum albumin, gamma globulin, and the like; prostaglandins; nucleic acids; carbohydrates; fats; narcotics such as morphine, codeine, and the like; psychotherapeutics; anti-malarials; L-dopa, diuretics such as furosemide, spironolactone, and the like; antiulcer drugs such as ranitidine HCl, cimetidine HCl, and the like.

Immunological agents that can be encapsulated by this method include, interleukins, interferon, colony stimulating factor, tumor necrosis factor, and the like; allergens such as cat dander, birch pollen, house dust mite, grass pollen, and the like; antigens of such bacterial organisms as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgdorferi, Campylobacter jejuni*, and the like; antigens of such viruses as smallpox, influenza A and B, respiratory syncytial, parainfluenza, measles, HIV, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Examples of non-biological agents that can be encapsulated by this method include, but are not limited to, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellents, solvents, stabilizers, polymer additives, and the like.

After the agent is added to the wall material/excipient solvent, the agent/(wall material-excipient)/solvent mixture dispersion is added to a continuous process medium to form microdroplets. This process medium is generally water, although organic solvents and oils can also be used when water is used to dissolve the wall material or excipient. The process medium preferably contains surfactants to allow the formation of a stable emulsion and prevent agglomeration. Examples of cationic, anionic, and nonionic compounds that can be used as surfactants include, but are not limited to, poly(vinyl alcohol), carboxymethyl cellulose, gelatin, poly(vinyl pyrrolidone), Tween 80, Tween 20, and the like. The concentration of surfactant in the process medium should be sufficient to stabilize the emulsion. The concentration of surfactant present will affect the final size of the microcapsules or microspheres. Generally the concentration of the surfactant in the process medium will be wall material/excipient from 0.1% to about 20% depending on the surfactant, the polymer solvent, and the processing medium used.

Prior to the addition of the mixture containing the dissolved wall material/excipient, its solvent and the agent, the process medium is saturated with the same solvent used to dissolve the wall material/excipient to prevent any extraction of solvent from the microdroplets during formation of the emulsion. The process medium is then mechanically agitated with devices such as homogenizers, propellers, or the like as the agent/wall material/solvent mixture is added to the process medium. During this step of the process, no solvent is evaporated or removed from the microdroplets. The temperature at which the emulsion is formed is not particularly critical, except that it must be within a range that will prevent the solvent from boiling or the process medium from gelling or freezing or the agent or wall material from degrading. The time required to form an emulsion is quite short. Generally, emulsions can be formed within 30 seconds to 5 minutes, depending upon the surfactant used and the method of agitation of the process medium.

As soon as an emulsion forms, all of the process medium containing the organic microdroplets is transferred, as quickly as possible, to an extraction medium so that greater than 20% to 30% of the solvent is immediately removed from the microdroplets (i.e., within 3 minutes). Normally, water is used as the extraction medium but other solvents or oils can also be used. In addition, salts may be added to the extraction medium to adjust its ionic strength or pH. The amount of extraction medium used is somewhat critical in that sufficient medium must be present to allow approximately immediate extraction of the solvent out of the microdroplets. Accordingly, the volume of the extraction medium will depend on the solvent used to dissolve the wall material and its solubility in the extraction medium. Generally, the volume of the extraction medium should be at least the volume needed to dissolve all of the solvent out of the microdroplets, preferably a volume 10-fold or higher.

After extraction of all or almost all of the solvent from the microdroplets (generally within 15 to 30 minutes), the hardened microcapsules or microspheres are collected by centrifugation, filtration, or the like. One advantage to this process is that it can be a discontinuous or a continuous process.

Having generally described the invention, certain processing parameters will now be described that affect the structure and properties of the final product. Generally, when solid compounds and in certain instances liquids are microencapsulated, the resultant product obtained are microspheres. Generally, when liquids are encapsulated, the liquid coalesces inside of the microdroplet resulting in a microcapsule product. If the liquid is removed, for example, by vacuum drying, from the microcapsule product, microbubbles can be obtained.

One of the advantages of the present invention is that solid agents can be encapsulated with the final product comprising microcapsules that demonstrate zero-order or near zero-order release kinetics. This is achieved by encapsulating very water-soluble agents; especially during formation of the emulsion, very water-soluble agents attract water into the microdroplet which coalesces and keeps the wall-forming material from precipitating as a matrix throughout the microdroplet. Obviously, to obtain a microcapsule, the solid agent being encapsulated must have sufficient water solubility to attract water into the microdroplet. If the active agent does not have the proper solubility, then coencapsulation of the agent with a highly water-soluble auxiliary compound such as a sugar or salt can result in the formation of microcapsules. Or if the sugar or salt is encapsulated only and subsequently removed from the microcapsules, microbubbles can be obtained.

Because water-soluble agents, such as peptides and proteins, do not diffuse through hydrophobic wall-forming materials such as the lactide/glycolide copolymers, pores must be created in the microcapsule or microsphere membrane to allow these agents to diffuse out for controlled-release applications. Several factors will affect the porosity obtained. The amount of agent that is encapsulated affects the porosity of microspheres. Obviously, higher-loaded microspheres (i.e., greater than about 20 wt. %, and preferably between 20 wt. % and 80 wt. %) will be more porous than microspheres containing smaller amounts of agent (i.e., less than about 20 wt. %) because more regions of drug are present throughout the microspheres. The ratio of agent to wall-forming material that can be incorporated into the microspheres can be as low as 0.1% to as high as 80%. Obviously, the loading that can be obtained for specific agents will depend to some extent on the physical properties of the agent and the desired application for the microsphere formulation.

The solvent used to dissolve the wall-forming material will also affect the porosity of the membrane. Microspheres or microcapsules prepared from a solvent such as ethyl acetate will be more porous than microspheres or microcapsules prepared from chloroform. This is due to the higher solubility of water in ethyl acetate than in chloroform. More specifically, during the emulsion step, no solvent is removed from the microdroplets because the process medium is saturated with solvent. Water, however, can dissolve in the solvent of the microdroplets during the emulsion step of the process. By selecting the appropriate solvent or cosolvents, the amount of continuous process medium that will dissolve in the microdroplets can be controlled, which will affect the final porosity of the membrane and the internal structure of the microspheres or microcapsules.

Another factor that will affect the porosity of the membrane is the initial concentration of the wall material/excipient in the solvent. High concentrations of wall material in the solvent result in less porous membranes than do low-concentrations of wall material/excipient. Also, high concentrations of wall material/excipient in the solvent improve the encapsulation efficiency of water-soluble compounds because the viscosity of the solution is higher. Generally, the concentration of wall-forming material/excipient in the solvent will range from about 3% to about 40%, depending on the physical/chemical properties of the wall material/excipient such as the molecular weight of the wall-forming material and the solvent used.

Having generally described the invention, a further understanding can be obtained by reference to certain specific examples which are provided herein for purpose of illustration only and are not intended to be limiting unless otherwise specified.

EXAMPLE 1

The following procedure was used to encapsulate choline chloride in polystyrene using an aqueous process medium. The solubility of choline chloride in water is greater than 3 grams per milliliter.

First, a polymer solution was prepared by dissolving 1.0 g of polystyrene (Type 6850, Dow Chemical Co.) in 9.0 g of methylene chloride. Next, 1.0 g of choline chloride was dissolved in 250 $\mu$L deionized water. The polystyrene solution was transferred to a 100-$\times$20-mm test tube. While the polystyrene solution was being vortexed, the choline chloride solution was added dropwise to the test tube. The choline chloride was homogeneously dispersed in the polystyrene solution by homogenization using a Brinkmann Polytron (Model 10, PTA-10S probe, speed setting of 5, Brinkmann Instruments Co., Westbury, N.Y.).

A 100-mL resin kettle was fitted with a truebore stirrer and a 1.5-in. TEFLON turbine impeller. Next, 50 mL of 4 wt. % aqueous poly(vinyl alcohol) (PVA) was saturated with 0.8 g of methylene chloride and transferred to the resin kettle. The polystyrene/choline chloride dispersion was poured directly into the PVA processing medium. During this transfer, the PVA solution was being stirred at about 550 rpm. After the resulting oil-in-water emulsion had stirred in the resin kettle for 1 min, the contents of the resin kettle were transferred all at once into 3.5 L of deionized water contained in a 4-L beaker and being stirred at about 750 rpm with a 2-in. stainless steel impeller. The resultant microspheres were stirred in the deionized water for about 25 min, collected over an 8-in diameter, 45-micron mesh stainless steel sieve, rinsed with 4 L of deionized water, and dried for 48 hours at ambient temperature in a vacuum chamber.

The final microsphere product consisted of free flowing spherical particles having diameters of about 45 to 250 microns and containing about 40 to 45 wt. % choline chloride.

EXAMPLE 2

A 15 wt. % polymer solution was prepared by dissolving 0.75 g of 50:50 poly(DL-lactide-co-glycolide) (DL-PLG) in 4.25 g of methylene chloride. Next 30 mg of formalinized staphylococcal enterotoxin B (SEB) was dissolved in 110 $\mu$L deionized water. The organic polymer solution was transferred to a 16$\times$100 mm test tube and the SEB toxoid solution was then introduced dropwise into the polymer solution while the latter was being agitated with a Vortex mixer. This mixture was then homogenized with a Polytron homogenizer to ensure that the SEB toxoid was homogeneously dispersed in the DL-PLG solution.

In a separate container, 300 mL of 1.5 wt. % aqueous carboxymethyl cellulose that had been saturated with methylene chloride was equilibrated to 19.0+/$-$1.0° C. The standard head, equipped with the emulsor screen, of a Silverson Laboratory Mixer was positioned below the surface of the carboxymethyl cellulose solution and the stir rate of the mixer was adjusted to approximately 4200 rpm.

The SEB toxoid/DL-PLG mixture was dispersed as microdroplets in the aqueous carboxymethyl cellulose. The resulting oil-in-water emulsion was stirred for about 3 minutes, after which the emulsion was transferred all at once to 3.5 L of deionized water contained in a glass beaker and being stirred at about 500 rpm with a 2-$\mu$m stainless steel impeller. The resultant microspheres were stirred in the purified water for about 20 min, collected over a 0.22-$\mu$m filter, and dried for 48 h in a vacuum chamber.

The resultant microsphere product consisted of spherical particles about 1 to 10 μm comprising 2.7 wt. % of SEB toxoid in poly(DL-lactide-co-glycolide).

EXAMPLE 3

Approximately 2.5 g of poly(DL-lactide)(DL-PL) was dissolved in the appropriate quantity of methylene chloride to prepare an 11.1 wt. % polymer solution. After the polymer was completely dissolved, a predetermined quantity of testosterone propionate was added and allowed to dissolve. This polymer/drug solution was then poured into a 1-L resin kettle containing 400 g of 5.0 wt. % PVA. The PVA was being stirred at about 750 rpm by a 2.5 in. TEFLON impeller driven by a Fisher Stedi-speed motor. The PVA was also saturated with 7 mL of methylene chloride prior to the addition of the polymer/drug solution. The resulting emulsion was allowed to stir for 7 min., after which the resin kettle contents were transferred all at once to 12.0 L of stirring deionized water. The microspheres were stirred in the deionized water for approximately 30 min and then were collected over 45-μm and 212-μm stainless steel mesh steel sieves arranged in series. The microspheres were rinsed with additional deionized water and allowed to air dry.

A similar batch of testosterone proprionate microspheres was made with a 20.6 wt. % polymer solution. The in vitro release rates for these two batches are shown below, demonstrating that the concentration of the polymer solution can be used to manipulate the release properties of microspheres. That is, higher polymer concentration gave slower releasing microspheres.

| Polymer solution concentration wt % | Core loading, wt % testosterone propionate | In vitro release, % at time | | | | | |
|---|---|---|---|---|---|---|---|
| | | 1 h | 1 d | 2 d | 3 d | 6 d | 8 d |
| 11.1 | 39.5 | 8.2 | 29.3 | 38.5 | 45.2 | 59.3 | 70.7 |
| 20.6 | 40.2 | 2.0 | 9.0 | 13.3 | 16.7 | 22.8 | 30.2 |

EXAMPLE 4

A 0.5-g amount of etretinate [(All-E)-9-(4-methoxy-2,3,6-trimethyl) phenyl-3,7-dimethyl-2,4,6,8-nonatetraenoic acid, ethyl ester] and 0.33 g of 50:50 DL-PLG were dissolved in 12.4 g of methylene chloride. (Due to the photosensitivity of etretinate, all steps in the process were done in the dark.) The organic solution was dispersed as microdroplets in 300 g of 10 wt. % aqueous poly(vinyl alcohol). The emulsion was obtained by the addition of the organic solution to a rapidly stirring solution of aqueous poly(vinyl alcohol) in a glass container. A Silverson Heavy Duty Laboratory Mixer was used to stir the emulsion.

After the organic microdroplets were stirred in the poly(vinyl alcohol) solution for 5 min to form a stable oil-in-water emulsion, the emulsion was transferred to 4 L of stirring, deionized water. The resultant microspheres were stirred in the deionized water for 30 min, separated from the poly(vinyl alcohol) by centrifugation, and collected by lyophilization.

The final product consisted of free-flowing particles with diameters from 0.5 to 5 μm containing 40 wt. % etretinate in poly poly(DL-lactide-co-glycolide).

EXAMPLE 5

A 12 wt. % polymer solution was prepared by dissolving 1.0 g of 50:50 DL-PLG in 7.3 g of methylene chloride. Next, 0.4 g amount of micronized cefazolin sodium was dispersed in the polymer solution. The cefazolin/polymer mixture was dispersed as microdroplets in 100 g of 6 wt. % of aqueous poly(vinyl alcohol) saturated with 2.4 g of methylene chloride. The emulsion was obtained by the addition of the cefazolin/polymer mixture to the aqueous poly(vinyl alcohol) solution while stirring the PVA at about 1000 rpm in a resin kettle. A TEFLON turbine impeller driven by a Fisher Stedi-Speed motor was used to stir the emulsion. As the emulsion was stirred, water entered the microdroplets (as observed under a microscope) and coalesced. After a stable oil-in-water emulsion had formed, the contents of the resin kettle were transferred all at once to 3.5 L of water stirring at 600 rpm to extract the methylene chloride from the microcapsules. After the extraction was complete, the microcapsules were allowed to settle. Microcapsules were collected over sieves then washed with at least 3 L of water. Microcapsules were placed in a vacuum at ambient temperatures to dry for at least 24 h.

The resultant microcapsule product consisted of spherical particles with a central core of cefazolin sodium encapsulated in an outer DL-PLG membrane.

EXAMPLE 6

A 15 wt. % polymer solution was prepared by dissolving 3 g of 50:50 DL-P1G in 17 g of methylene chloride. Next, 0.4 g of LHRH was dispersed in the polymer solution while the latter was being agitated with a Polytron homogenizer. The LHRH/DL-PLG mixture was dispersed as microdroplets in 200 g of 5 wt. % poly(vinyl alcohol) (PVA) which had previously been saturated by adding 3.6 g of methylene chloride to the PVA. The emulsion was obtained by the addition of the LHRH/DL-PLG mixture to the PVA process medium being stirred at 1060 rpm and contained in a resin kettle. A TEFLON turbine impeller driven by a Fisher Stedi-Speed motor was used to stir the emulsion.

After a stable oil-in-water emulsion was formed, the emulsion was transferred all at once to 7 L of stirring deionized water to extract the methylene chloride. The resultant microspheres were allowed to harden in the water bath for 15 min, collected over 45 and 150 micrometer sieves, washed with approximately 2 L of deionized water to remove any residual PVA, and air dried for 48 h.

The final product consisted of a free-flowing powder with diameters ranging from 45 to 150 μm comprising 8.2 wt. % LHRH encapsulated in DL-PLG.

EXAMPLE 7

An 8 wt. % ethyl cellulose solution was prepared by dissolving 1 g of Ethocel (Premium grade, Standard ethoxy content, 20 viscosity, Dow Chemical Co., Midland, Mich.) in 11.5 g of methylene chloride. Next, 0.5 g of mannitol was dissolved in 3 mL of deionized water. The ethyl cellulose solution was transferred to a 100-×20-mm test tube. While the ethyl cellulose solution was being agitated with vortex mixer, the mannitol solution was added dropwise to the tube. A Brinkmann Polytron (Model 10, PTA-10S probe, speed setting of 5, Brinkmann Instruments Co., Westbury, N.Y.) was then used to homogenize the solution.

A 16-oz., wide-mouth jar was used to contain 300 mL of a 5 wt. % aqueous solution of (PVA). This solution was saturated with 4.8 g of methylene chloride. Throughout the procedure the PVA solution was maintained at 19° C. A Silverson Laboratory Mixer Emulsifier (Model L2R, equipped with a medium emulsor screen, Silverson Machines Limited, Waterside, Chesham, Buckinghamshire, England) was used to stir the PVA solution at 4000 rpm. Using a 10 mm bore funnel, the ethyl cellulose/mannitol solution was added to of the stirring PVA. After 4 min, the contents of the jar were transferred all at once to 3 L of deionized water stirring at about 750 rpm. The methylene chloride was extracted into the water along with the mannitol to give microbubbles. The microbubbles were stirred for 1 h to ensure that all of the mannitol and methylene chloride was removed. The microbubbles were then collected.

The final microbubble product consists of spherical particles 1 to 10 microns in diameter with a hollow interiors.

EXAMPLE 8

An 11.9 wt. % polymer solution was prepared by dissolving 0.5 g of 52.48 poly(DL-lactide-co-glycolide) (DL-PLG) (inherent viscosity of 0.73 dL/g, measured at a polymer concentration of 0.5 g/dL in hexafluoroisopropanol at 30° C. using a Cannon viscometer) in 3.7 g of methylene chloride. Next, 0.125 g of a mixture comprising 1 part by weight of interleukin-2 conjugated to a polyol polymer (PEG-IL-2) and 20 parts by weight of human serum albumin was weighed into a 16×75 mm test tube. The DL-PLG solution was added to the test tube, and the mixture was homogenized three times for 30 sec, with 15-sec intervals between homogenations. The homogenization was done with a Brinkman Polytron (Model 10, PTA-10S probe, speed setting of 6).

A 200-mL resin kettle was fitted with a truebore stirrer and a 1.5-in. TEFLON turbine impeller. Next, 150 mL of 6 wt. % aqueous poly(vinyl alcohol) was saturated with 2.4 g of methylene chloride and transferred to the resin kettle. The homogenized organic mixture was dispersed as microdroplets in the poly(vinyl alcohol). The dispersion was obtained by the addition of the organic mixture beneath the surface of the poly(vinyl alcohol) solution. During this transfer, the poly(vinyl alcohol) was being stirred at about 1000 rpm. The dispersion was stirred in the resin kettle for 5 min resulting in the formation of a stable oil-in-water emulsion.

After a stable oil-in-water emulsion was prepared, the contents of the resin kettle were quickly transferred to 10 L of deionized water contained in a 12-L beaker and being stirred at about 800 rpm with a 2-in. stainless steel impeller. The resultant microspheres were stirred in the deionized water for about 15 min, collected over an 8-in diameter, 45-μm stainless steel sieve, rinsed with 4 L of deionized water, and dried for 48-h at ambient temperature in a vacuum chamber. The final product consisted of free-flowing particles with diameters from 45 to 200 μm comprising 15.6 wt. % of the PEG-IL-2/HSA mixture in poly(DL-lactide-co-glycolide).

What is claimed is:

1. An emulsion-based method of microencapsulating an agent to form a microencapsulated product, comprising the steps of:

a) dissolving or dispersing an effective amount of said agent in a solvent containing a dissolved wall forming material to form a dispersion;
   b) combining said dispersion with an effective amount of a continuous process medium to form an emulsion that contains said process medium and microdroplets comprising said agent, said solvent and said wall forming material; and
   c) immediately after the formation of said emulsion, adding all at once said emulsion to an effective amount of an extraction medium to extract said solvent from said microdroplets to form said microencapsulated product, wherein said solvent has a solubility of from about 1 part per 100 parts to about 25 parts per 100 parts in said extraction media.

2. The method of claim 1, wherein said adding step comprises the addition of said emulsion to said extraction medium within 3 minutes.

3. The method of claim 1, wherein said dispersing step comprises dissolving said agent in said solvent.

4. The method of claim 1, wherein said solvent is immiscible with said process medium.

5. The method of claim 1, wherein said process medium is water.

6. The method of claim 1, wherein said process medium is an organic solvent.

7. The method of claim 1, wherein said process medium is an oil.

8. The method of claim 1, wherein said process medium contains a surfactant.

9. The method of claim 8, wherein said surfactant is present in the process medium from about 0.1% to about 20% by weight.

10. The method of claim 1, and further comprising the step of saturating said process medium with said solvent prior to said step of adding said dispersion to said continuous process medium.

11. The method of claim 1, and further comprising the step of preventing the evaporation of said solvent from said microdroplets.

12. The method of claim 1, wherein said extraction medium is water.

13. The process of claim 1, wherein said extraction medium is an organic solvent.

14. The method of claim 1, wherein said extraction medium is an oil.

15. The method of claim 1, and further comprising the step of dissolving an effective amount of a salt in said extraction medium to adjust its ionic strength.

16. The method of claim 1, and further comprising the step of controlling the pH of said extraction medium by adding an acid or base.

17. The method of claim 1, and further comprising the step of separating said microencapsulated product from said extraction medium.

18. The method of claim 1, wherein said agent is a highly water soluble compound.

19. The method of claim 1, wherein said agent has a solubility of greater than 10 milligrams per milliliter in said continuous process medium.

20. The method of claim 1, wherein the ratio of said agent to said wall forming material in said dispersion is high to affect the porosity of said microencapsulated product.

21. The method of claim 1, wherein the percentage of said agent to said wall forming material in said dispersion is greater than 20 wt. %.

22. The method of claim 1, wherein the percentage of said agent to said wall forming material in said dispersion is from about 20 wt. % to about 80 wt. %.

23. The method of claim 1, wherein the percentage of said agent to said wall forming material in said dispersion is low to affect the porosity of said microencapsulated product.

24. The method of claim 1, wherein the percentage of said agent to said wall forming material in said dispersion is less than 20 wt. %.

25. The method of claim 1, wherein said continuous process medium is soluble in said solvent to control the porosity of said microencapsulated product.

26. The method of claim 1, wherein said continuous process medium has a solubility of from about 2% to about 25% in said solvent to provide said microencapsulated product with a high porosity.

27. The method of claim 1, wherein said continuous process medium has a solubility of less than about 2% in said solvent.

28. The method of claim 1, wherein said solvent is selected from the group consisting of ethyl acetate, diethyl carbonate, chloroform and methylene chloride and said continuous process medium is water.

29. The method of claim 1, wherein said agent is soluble in said continuous process medium.

30. The method of claim 1, wherein said agent has a solubility greater than 100 mg/mL in said continuous process medium.

31. The method of claim 1, and further comprising the step prior to step b) of mixing a water soluble auxiliary compound with said agent.

32. The method of claim 31, wherein said auxiliary compound has a solubility greater than 100 mg/mL in said continuous process medium.

33. The method of claim 31, wherein said auxiliary compound has a solubility greater than 1 gram/mL in said continuous process medium.

34. The method of claim 31, wherein said agent is a solid compound.

35. The method of claim 34, wherein said microcapsule exhibits zero-order release kinetics.

36. The method of claim 31, wherein said auxiliary compound has a solubility greater than 100 mg/mL in said extraction medium.

37. The method of claim 31, wherein said auxiliary compound has a solubility greater than 1 gram/mL in said extraction medium.

38. The method of claim 1, wherein said agent is a solid compound.

39. The method of claim 1, wherein said agent is a liquid.

40. The method of claim 1, wherein the percentage of wall forming material to solvent in said dispersion is between about 3 wt. % and 40 wt. %.

41. The method of claim 1, wherein said agent is removed from said microencapsulated product during or after said extraction of said solvent from said microdroplets to provide a microbubble.

42. The method of claim 41, wherein said agent is a solid having a solubility over 1 gram/mL in said continuous process medium.

43. The method of claim 41, wherein said agent is a liquid.

44. The method of claim 43, wherein said liquid is mannitol dissolved in water.

45. The method of claim 1, wherein said wall-forming material is present at a concentration greater than 20 wt. % in said solvent.

46. The method of claim 45, wherein said agent is a solid having a solubility over 1 gram/mL in said extraction medium.

47. The method of claim 1, wherein said wall-forming material is present at a concentration less than 20 wt. % in said solvent.

48. The method of claim 1, wherein said agent has a solubility of greater than 10 milligrams per milliliter in said extraction medium.

49. The method of claim 1, wherein said agent has a solubility greater than 100 mg/mL in said extraction medium.

50. The method of claim 1, wherein said method comprises a continuous process.

51. The method of claim 1, wherein the microencapsulated agent is an analgesic, anesthetic, anorexic, antiarthritic, antiasthmatic, antibiotic, antifungal, antiviral, anticancer agent, anticoagulant, anticonvulsant, antidepressant, antihistamine, hormone, tranquilizer, antispasmodic, vitamin, mineral, cardiovascular agent, enzyme, peptide, protein, prostaglandin, nucleic acid, carbohydrate, fat, narcotic, psychotherapeutic, antimalarial, L-dopa, diuretic, antiulcer drug, or immunological agent.

52. The method of claim 1, wherein the microencapsulated agent is an adhesive, pesticide, fragrance, antifoulant, dye, salt, oil, ink, cosmetic, catalyst, detergent, curing agent, flavor, food, fuels, herbicides, metal, paint, photographic agent, biocide, pigment, plasticizer, propellant, solvent, stabilizer or polymer additive.

53. The method of claim 1, wherein the wall-forming material is poly(lactide), poly(glycolide), poly(caprolactone), poly(hydroxybutyrate) or copolymers thereof.

54. The method of claim 1, wherein the microencapsulated product comprises a central core comprising said agent surrounded by an outer membrane.

55. The method of claim 1, wherein the diameter of said microencapsulated product ranges from nanoparticles to about 2 millimeters.

56. The method of claim 1, wherein the diameter of said microencapsulated product ranges from about 1 μm to about 10 μm.

57. The method of claim 1, wherein the diameter of said microencapsulated product ranges from about 1 μm to about 5 μm.

58. The method of claim 1, wherein the diameter of said microencapsulated product ranges from about 5 μm to about 10 μm.

59. The method of claim 1, wherein the diameter of said microencapsulated product ranges from about 45 μm to about 250 μm.

60. A method of preparing a microencapsulated product having an encapsulating wall exhibiting high porosity, wherein the encapsulated agent is soluble in a continuous process medium, an extraction medium, or both media, comprising the steps of:
   a) dissolving or dispersing said agent in a solvent containing a dissolved wall forming material to form a dispersion; the percentage of said agent to said wall forming material being greater than about 20 wt. %;
   b) combining said dispersion with an effective amount of said continuous process medium to form an emulsion that contains said process medium and microdroplets comprising said agent, said solvent and said wall forming material; and c) immediately after the formation of said emulsion, adding all at once alter step b) said emulsion to an effective amount of said extraction medium to extract said solvent from said microdroplets to form said microencapsulated product, wherein said solvent has a solubility of from about 1 part per 100 parts to about 25 parts per 100 parts in said extraction medium.

61. The method of claim 60, wherein said continuous process medium is highly soluble in said solvent.

62. The method of claim 61, wherein said continuous process medium has a solubility of from about 2% to about 25% in said solvent.

63. The method of claim 60, wherein the percentage of said agent to said wall forming material in said dispersion is from about 20 wt. % to about 80 wt. %.

64. A method of preparing a microencapsulated product having an encapsulating wall exhibiting low porosity, wherein the encapsulated agent is soluble in a continuous process medium, and extraction medium, or both media, comprising the steps of:

a) dissolving or dispersing said agent in a solvent containing a dissolved wall forming material to form a dispersion; the percentage of said agent to said wall forming material being less than about 20 wt. %;

b) combining said dispersion with an effective amount of said continuous process medium to form an emulsion that contains said process medium and microdroplets comprising said agent, said solvent and said wall forming material; and c) immediately after the formation of said emulsion, adding all at once after step b) said emulsion to an effective amount of said extraction medium to extract said solvent from said microdroplets to form said microencapsulated product, wherein said solvent has a solubility of from about 1 part par 100 parts to about 25 parts per 100 parts in said extraction medium.

65. The method of claim 64, wherein said continuous process medium has a solubility of less than about 2% in said solvent.

66. A method of preparing a microencapsulated product having an encapsulating wall exhibiting high porosity, wherein the encapsulated agent is soluble in a continuous process medium, and extraction medium, or both media, comprising the steps of:

a) dissolving or dispersing said agent in a solvent containing a dissolved wall forming material to form a dispersion;

b) combining said dispersion with an effective amount of said continuous process medium to form an emulsion that contains said process medium and microdroplets comprising said agent, said solvent and said wall forming material, said continuous process medium having a solubility of from about 2% to about 25% in said solvent; and c) immediately after the formation of said emulsion, adding all at once after step b) said emulsion to an effective amount of said extraction medium to extract said solvent from said microdroplets to form said microencapsulated product, wherein said solvent has a solubility of from about 1 part per 100 parts to about 25 parts per 100 parts in said extraction medium.

67. A method of preparing a microencapsulated product having an encapsulating wall exhibiting low porosity, wherein the encapsulated agent is soluble in a continuous process medium, and extraction medium, or both media, comprising the steps of:

a) dissolving or dispersing said agent in a solvent containing a dissolved wall forming material to form a dispersion;

b) combining said dispersion with an effective amount of said continuous process medium to form an emulsion that contains said process medium and microdroplets comprising said agent, said solvent and said wall forming material, said continuous process medium having a solubility of less than about 2% in said solvent; and c) immediately after the formation of said emulsion, adding all at once after step b) said emulsion to an effective amount of said extraction medium to extract said solvent from said microdroplets to form said microencapsulated product, wherein said solvent has a solubility of from about 1 part per 100 parts to about 25 parts per 100 parts in said extraction medium.

68. A method of microencapsulating an agent from media in which said agent is soluble, to form a microencapsulated product, comprising the steps of:

a) dissolving or dispersing an effective amount of said agent in a solvent containing a dissolved wall forming material to form a dispersion;

b) combining said dispersion with and effective amount of a continuous process medium to form an emulsion that contains said process medium and microdroplets comprising said agent, said solvent and said wall forming material, wherein said agent is soluble in said continuous process medium; and c) immediately after the formation of said emulsion, adding all at once said emulsion to an effective amount of an extraction medium to extract said solvent from said microdroplets to form said microencapsulated product, wherein said agent is soluble in said extraction medium, wherein said solvent has a solubility of from about 1 part per 100 parts to about 25 parts per 100 parts in said extraction medium.

69. A method of microencapsulating an agent, to form a microencapsulated product, comprising the steps of:

a) dissolving or dispersing an effective amount of said agent in a solvent containing a dissolved wall forming material to form a dispersion;

b) combining said dispersion with and effective amount of a continuous process medium to form an emulsion that contains said process medium and microdroplets comprising said agent, said solvent and said wall forming material, wherein said agent is soluble in said continuous process medium; and c) immediately after the formation of said emulsion, adding all at once said emulsion to an effective amount of an extraction medium to extract said solvent from said microdroplets to form said microencapsulated product, wherein said solvent has a solubility of from about 1 part per 100 parts to about 25 parts per 100 parts in said extraction medium.

70. A method of microencapsulating an agent from media in which said agent is soluble, to form a microencapsulated product, comprising the steps of:

a) dissolving dispersing an effective amount of said agent in a solvent containing a dissolved wall forming material to form a dispersion;

b) combining said dispersion with and effective amount of a continuous process medium to form an emulsion that contains said process medium and microdroplets comprising said agent, said solvent and said wall forming material; and c) immediately after the formation of said emulsion, adding all at once said emulsion to an effective amount of an extraction medium to extract said solvent from said microdroplets to form said microencapsulated product, wherein said agent is soluble in said extraction medium, wherein said solvent has a solubility of from about 1 part per 100 parts to about 25 parts per 100 parts in said extraction medium.

71. An emulsion-based method of microencapsulating an agent that is soluble in a continuous process medium, an extraction medium, or both media, to form a microencapsulated product comprising a central core of said agent surrounded by an outer membrane, comprising the steps of:

a) dissolving or dispersing an effective amount of said agent in a solvent containing a dissolved wall forming material to form a dispersion;

b) combining said dispersion with an effective amount of said continuous process medium to form an emulsion that contains said process medium and microdroplets comprising said agent, said solvent and said wall forming material; and c) immediately after the formation of said emulsion, adding all at once said emulsion to an effective amount of said extraction medium to extract said solvent from said microdroplets to form said microencapsulated product, wherein said solvent has a solubility of from about 1 part per 100 parts to about 25 parts per 100 parts in said extraction medium.

72. An emulsion based method of microencapsulating a water-soluble agent to form a microencapsulated product, comprising the steps of:

a) dissolving or dispersing an effective amount of said water-soluble agent in a solvent containing a dissolved wall forming material to form a dispersion;

b) combining said dispersion with an effective amount of an aqueous continuous process medium to form an emulsion that contains said aqueous process medium and microdroplets comprising said water-soluble agent, said solvent and said wall forming material; and c) immediately after the formation of said emulsion, adding all at once said emulsion to an effective amount of an aqueous extraction medium to extract said solvent from said microdroplets to form said microencapsulated product, wherein said solvent has a solubility of from about 1 part per 100 parts to about 25 parts per 100 parts in said extraction medium.

73. An emulsion-based method of microencapsulating an agent that has a propensity to partition within minutes into the continuous phase of the emulsion to form a microencapsulated product, comprising the steps of:

a) dissolving or dispersing an effective amount of said agent in a solvent containing a dissolved wall forming material to form a dispersion;

b) combining said dispersion with an effective amount of a continuous process medium to form an emulsion that contains said process medium and microdroplets comprising said agent, said solvent and said wall forming material, wherein said agent has a propensity to partition within minutes into said continuous process medium; and c) immediately after the formation of said emulsion, adding all at once said emulsion to an effective amount of an extraction medium to extract said solvent from said microdroplets to form said microencapsulated product, wherein said solvent has a a solubility of from about 1 part per 100 parts to about 25 parts per 100 parts in said extraction medium.

* * * * *